(12) United States Patent
Osarogiagbon

(10) Patent No.: US 10,422,801 B2
(45) Date of Patent: *Sep. 24, 2019

(54) LYMPH NODE SPECIMEN COLLECTION KIT

(71) Applicant: Raymond U Osarogiagbon, Memphis, TN (US)

(72) Inventor: Raymond U Osarogiagbon, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/942,830

(22) Filed: Apr. 2, 2018

(65) Prior Publication Data

US 2018/0259529 A1  Sep. 13, 2018

Related U.S. Application Data

(62) Division of application No. 13/448,091, filed on Apr. 16, 2012.

(60) Provisional application No. 61/475,522, filed on Apr. 14, 2011.

(51) Int. Cl.
*G01N 33/574* (2006.01)
*A61B 10/00* (2006.01)
*B01L 3/00* (2006.01)
*B01L 99/00* (2010.01)

(52) U.S. Cl.
CPC ... *G01N 33/57423* (2013.01); *A61B 10/0096* (2013.01); *B01L 3/508* (2013.01); *B01L 99/00* (2013.01)

(58) Field of Classification Search
CPC ............ B01L 99/00; B01L 3/00; A61B 10/00; G01N 33/574
See application file for complete search history.

(56) References Cited

U.S. PATENT DOCUMENTS

| | | |
|---|---|---|
| 2003/0130593 A1 | 7/2003 | Gonzalez |
| 2003/0216730 A1 | 11/2003 | Barry et al. |
| 2003/0219768 A1 | 11/2003 | Beebe et al. |
| 2005/0137591 A1 | 6/2005 | Barry et al. |
| 2007/0237373 A1 | 10/2007 | Kiraly et al. |
| 2009/0258350 A1 | 10/2009 | Morrison et al. |
| 2009/0287080 A1 | 11/2009 | Nishina et al. |
| 2009/0291449 A1 | 11/2009 | Knapp et al. |
| 2010/0049162 A1 | 2/2010 | Hameed |

FOREIGN PATENT DOCUMENTS

WO  0047710 A1  8/2000

OTHER PUBLICATIONS

Bar et al. Cervical Mediastinoscopic Lymphadenectomy for Accurate Staging in Lung Cancer, Asian Cadiovasc. Thorac. Ann. 2009; 17:357-61.
Collection Kit. Collection and Transport Kits. Therapak Cor.. 2007; 1-4.
Ko et al. "Pictorial Essay: CT Depiction of Regional Nodal Stations for Lung Cancer Staging." Amer. J of Roentgen., Mar. 1, 2000 (Mar. 1, 2000), vol. 174, No. 3, pp. 775-782.
Lardinois et al. ESTA Guidelines for Intraoperative Lymph Node Staging in Non-Small Cell Lung Cancer. EUR. J of Carido-Thorascic Sur. 2006: 30: 878-9792.
Penzel et al. "lymph Node Size and Metastatic infiltration in Non-Small Cell Lung Cancer." Chest J, Feb. 1, 2003 (Feb. 1, 2003) , vol. 123, iss 2, pp. 463-467.
Surgical Pathology. Surgical Pathology. Pathology Laboratories 2010;1.
Molnar, A new device for the Identification of Lymph Nodes at Lung Cancer Surgery, EUR. J. of Cardio-Thoracic Sur. V. 31, pp. 311-312 (2007).

*Primary Examiner* — Lynn Y Fan
(74) *Attorney, Agent, or Firm* — Veritay Group IP; Susan B. Fentress

(57) ABSTRACT

A unique system for the correlation between removed lymph nodes for lung cancer diagnosis and pathological analysis thereof is provided. Such a system includes the removal of certain lymph nodes from a suspected or known lung cancer patient with subsequent categorization thereof and placement within a properly divided and labeled specimen collection kit. Through the utilization of such a separation and placement allows and facilitates understanding and non-verbal communication between a surgeon and a pathologist in order to denote the location of the removed lymph nodes in relation to a known or suspected lung cancer tumor or growth. The overall diagnostic method, including the important communicative properties accorded both the particular surgeon and pathologist, is encompassed within this invention, as well as the specific collection specimen kit that permits the surgeon proper distinction of specific removal lymph nodes in relation to their location within the patient's body.

9 Claims, 9 Drawing Sheets

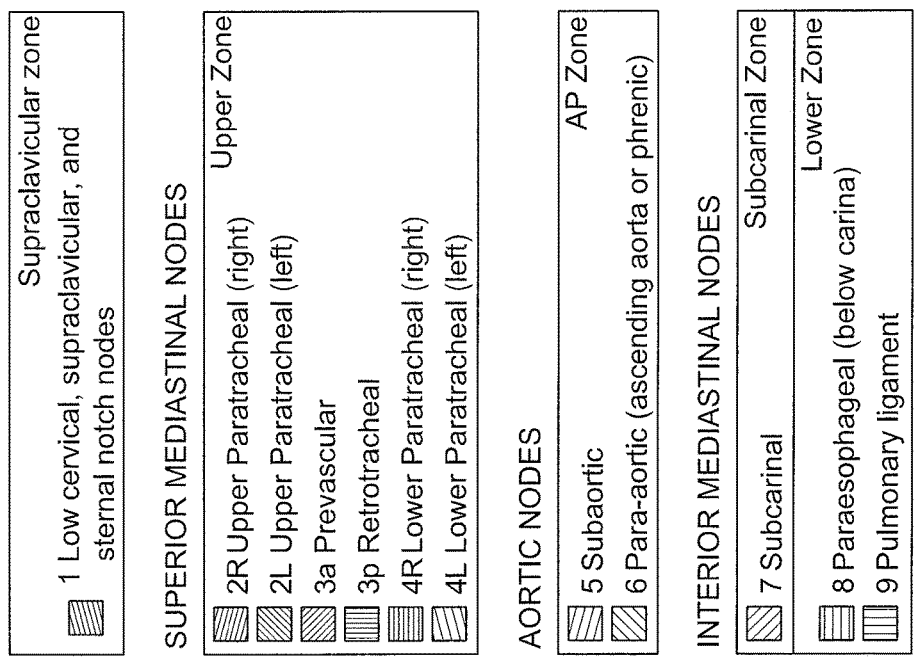
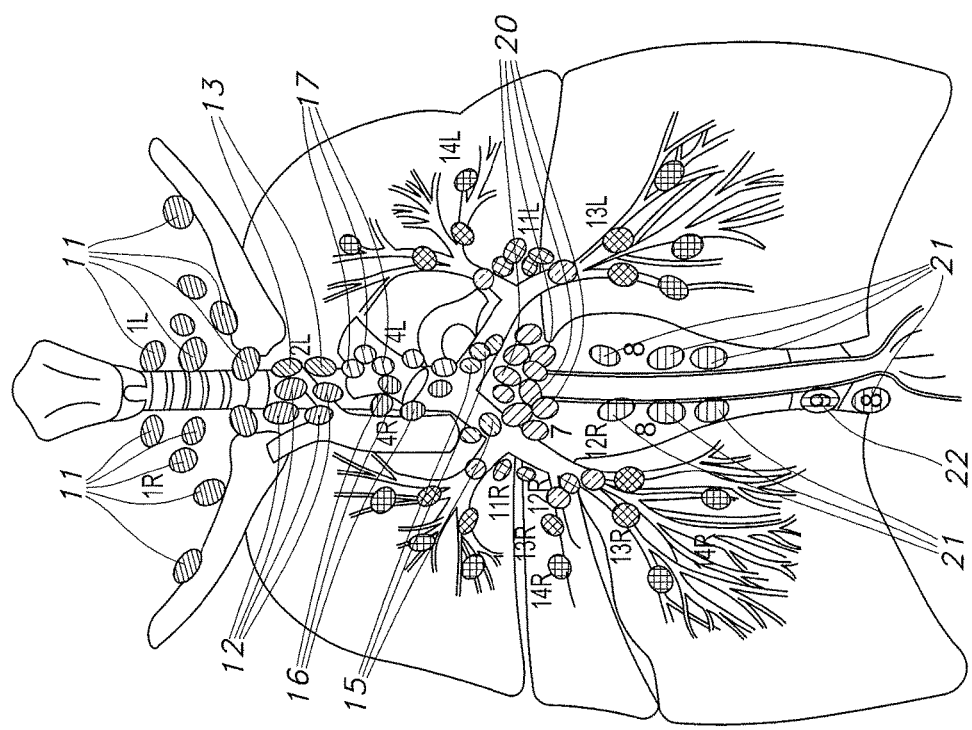
FIG. 1

LYMPH NODE SPECIMEN COLLECTION KIT

CROSS REFERENCE TO RELATED APPLICATIONS

This application is a divisional application of U.S. Ser. No. 13/448,091 filed 16 Apr. 2012 (hereby specially incorporated here by reference).

REFERENCE TO CORRELATED PATENT APPLICATION

This application is a conversion of and claims priority to U.S. Provisional Patent Application No. 61/475,522, filed on Apr. 14, 2011. The specification and drawings of such prior Provisional application are hereby entirely incorporated within.

FIELD OF THE INVENTION

A unique system for the correlation between removed lymph nodes for lung cancer diagnosis and pathological analysis thereof is provided. Such a system includes the removal of certain lymph nodes from a suspected or known lung cancer patient with subsequent categorization thereof and placement within a properly divided and labeled specimen collection kit. Through the utilization of such a separation and placement allows and facilitates understanding and non-verbal communication between a surgeon and a pathologist in order to denote the location of the removed lymph nodes in relation to a known or suspected lung cancer tumor or growth. In such a manner, the pathologist is provided a reliable means to assess the spread of cancerous cells throughout the thoracic region of the patient to provide a more thorough and direct diagnosis as to the necessary treatment regimen such a patient should undertake. The overall diagnostic method, including the important communicative properties accorded both the particular surgeon and pathologist, is encompassed within this invention, as well as the specific collection specimen kit that permits the surgeon and pathologist proper distinction of specific removed lymph nodes in relation to their location within the patient's body.

BACKGROUND OF THE INVENTION

Cancer has proven to be a very difficult disease to treat, as the abnormal growth of cells within different regions of a human body can be difficult to pinpoint in terms of severity and growth pattern and rate. In particular, lung cancer has proven to be particularly puzzling in terms of effective treatment due to the problems inherent in diagnosing the type and degree of abnormal growth present. In the past, drastic measures, including partial or even total lung removal has been a typical treatment in order to prevent further migration and growth of carcinomas and other dangerous cells throughout a patient's thoracic region. Additionally, through introduction into the lymphatic system, such cancerous cells can spread throughout the human body at an alarming rate. The earlier a proper diagnosis can be made as to the type and extent of spread of such dangerous cells, particularly within the lungs and associated draining lymph nodes, certainly the better.

One manner of at least attempting to diagnose the severity of cancer growth has been the removal of lymph nodes within the mediastinal region in order to assess the spread throughout the local lymphatic region of the patient. Unfortunately, however, there has been a significant disconnect between the surgeon and the pathologist, most pronounced in the lack of proper and specific lymph node removal by the surgeon in terms of actual locations from within the subject patient's mediastinal region and the thorough, correct, and complete examination of such surgically removed specific lymph nodes prior to removal by the pathologist. In the past, a surgeon would simply remove a cluster of lymph nodes together without any consideration as to the specific type in terms of location within the patient's lungs and mediastinum. Such a cluster would not, then, take account nor supply any further information for the pathologist in terms of actual mediastinal disposition within the subject patient. Furthermore, the lobes of lymph nodes provided the pathologist would be picked apart by the pathologist, generally, in order to analyze each individual removed lymph node for cancer indications. Hence, the pathologist could easily misplace such small (less than 3 cm long and wide, for instance) lymph nodes during and after analysis, and, without knowing the actual location of each removed lymph node, the pathologist would be limited in terms of the ability to pinpoint the specific growth rate and spread throughout the patient's mediastinal region. To date, although the different types of lymph nodes present within a typical patient's mediastinal area are well known and well defined, there has been no development or consideration given to the proper individual removal and subsequently analysis thereof of each and every mediastinal lymph node type. Without such a formal understanding and consideration of the actual location (and thus distances between subject lymph nodes), the pathologist lacks an important tool in providing the most comprehensive diagnosis the oncologist may then rely upon for most effective treatment to be provided the patient after surgery.

Compounding such a lack of consideration of such an important lymph node location issue is the lack of any tool that provides the surgeon a proper and reliable means to actually permit separation of individual mediastinal lymph nodes from a patient and properly store the same for the benefit of the pathologist to properly analyze each different type of lymph node removed for such a purpose. Thus, the present invention overcomes these three distinct issues: 1) to improve surgeon performance of lymphatic dissection/surgery; and 2) to improve communication between a surgeon and a pathologist to properly ascribe the extent of cancerous growth and/or migration from the patient's lungs through the mediastinum; and 3) to improve pathologist examination overall through a proper label and consideration of each removed lymph node specimen in relation to its initial proximity to a patient's lungs.

Advantages and Summary of the Invention

Thus, one distinct advantage of this inventive method and specimen collection kit is the capability of directing a lymph node removing surgeon to properly assess the specific locations of each removed lymph node for comparison with every other removed lymph node by a pathologist. Also, one advantage of this invention is the ease for a pathologist to merely remove each lymph node sample from a properly coded specimen container and consider the location of such a lymph node as one portion of their overall lung cancer diagnosis and staging (i.e., determining the extent of spread).

Accordingly, this invention encompasses a method of lung cancer diagnosis based upon the consideration of cancerous growth within specific types of lymph nodes present within a subject patient's mediastinal region, wherein said method includes the steps of:

A) supplying a specimen collection kit including separate collection containers, wherein each collection container is coded in some manner associated with a specific station of each and every lymph node to be removed from the subject patient's mediastinal region and placed within each suitably coded collection container;

B) having a surgeon (or like physician) remove at least one lymph node from each specifically pre-identified coded mediastinal station of said patient;

C) having the surgeon place each removed lymph node within its appropriately coded (such as through associated color, station name, and/or station number) collection container, thereby indicating each different type of removed lymph node present within the collection container bottles in relation to the actual mediastinal location from which each of said removed lymph nodes was present; and D) providing a pathologist with said collection containers including the properly coded removed lymph nodes in order to permit analysis of each removed lymph node for degree of cancerous growth and/or activity in relation to the mediastinal location of each such lymph node and in relation to any known cancerous growths within the same mediastinal area.

The specimen collection kit including appropriately coded collection containers into which a surgeon will deposit specific lymph nodes in accordance with their station within a target patient's mediastinal region is also encompassed within this invention. Such containers may be removable from such a kit or integrated permanently therein. As noted above, the coding of such containers may be of any type that properly distinguishes a specimen in terms of its removal location from within a patient's mediastinal region. Thus, a color (with a different one ascribed to each station), a station name, and/or a station number, may be utilized for such a purpose with the desire to have the pathologist fully comprehend each separate container for such a purpose without any trouble. As such, although only one type of code may be utilized for this purpose, in actuality, the overall system may include any number of combinations of coding (again, color, name, number, as examples, with all three potentially preferred for such a result) in place to facilitate identification by the surgeon for initial placement and the pathologist for subsequent removal and proper analysis and examination. Thus, such a kit allows for such proper deposit by a surgeon as well as proper analysis and examination by a pathologist in terms of such the specific station of each lymph node present therein. The collection containers themselves do not require a large volume for such a purpose (a typical, non-limiting size of container is 5 cm height by 3.8 cm diameter, with a removal lid, and 4.7 cm height by 3.8 cm diameter, without a removal lid in place). The deposited and stored node material is placed and kept within a proper preservative liquid, such as formalin and/or saline, to ensure such removed nodes will not disintegrate at a rapid rate prior to pathological examination.

The stations for such lymph node removal are twelve (12) in number, as described in greater detail below. Such sequestration of removed nodes into distinct specimen containers facilitates communication between the surgeon and pathologist such that proper examination of the extent of cancer spread in relation to these mediastinal stations can be accomplished. As noted above, there is currently no system that provides such needed separation of removed lymph nodes to properly allow for pathologist comprehension and understanding of their prior location within the patient's body. Since the lymph nodes generally have the same appearance, regardless of station within the patient's mediastinal region, without any manner to properly distinguish such specimens, the surgeon would be required to communicate such station information directly with the pathologist in the past in order to provide the necessary degree of depth of understanding for a more robust analysis of the overall condition of the patient. Thus, through the utilization of twelve separate specimen containers, properly coded for definitive stations within the patient's mediastinal region, such desired-for, simplified, and reliable communication of information between the subject surgeon and the examining pathologist. The specimen containers may be placed within or integrated into an easy-to-transport, as well as safe-to-transport, kit, such as within a box with proper openings for placement of the specimen containers or wells present to act as the specimen containers, as non-limiting examples, wherein the box has a lid (which may be fitted to any degree, from loosely placed to hermetically sealed) to keep such containers in place during transport, etc. Alternatively, the kit may be split into two separate boxes with one including nodes removed from the right side of the subject patient's mediastinal region (and lungs), and the other box including containers with specimen nodes from the patient's left side.

The internal arrangement of the kit itself may be of any manner that allows for the comprehension by the pathologist of the proper codes utilized for the different stations of lymph node removal. Thus, the containers may be configured in numeric order, in relation to their station locations, or even randomly, again, as long as the pathologist can easily determine the codes involved (and, presumably, that the surgeon placed the specific removed nodes within the properly coded specimen containers initially).

Additionally, the kit may include a checklist for either or both of the surgeon and pathologist to follow in relation to their respective contributions to the overall diagnostic procedure involved. For instance, the kit may provide a list of mandatory lymph node stations that require removal of specimens by the surgeon. As well, such instructions may further provide a manner of indicating any reasons the surgeon did not follow such a desired protocol (and can be completed by any member of the operating room team, if necessary). Basically, the overall diagnostic system and process allows for more than just communication between operating room and pathology lab through the placement and transport of properly coded specimen containers, particularly if there is a need to avoid removal of certain nodes from certain stations of the patient's mediastinal region. The pathologist may thus also provide an indication as to the lack of necessity for examining any specimen received in this manner. The important issue is that the overall procedure permits reliable communication of specimen removal stations for more robust examination and, hopefully, more reliable diagnosis of lung cancer spread within a subject patient.

As noted above, the typical manner of lymph node removal in the past was through the simultaneous removal of clusters of lymph nodes without any distinction in terms of the specific location of each node within an effected lung (or surrounding areas). The nodes themselves do not differ to any appreciable degree in appearance and, as such, clusters of nodes would provide a pathologist with a rather limited capability of diagnosing general results in terms of cancer spread, rather than allowing for specifics in terms of actual degree of cancer growth throughout the mediastinal region. The lack of a system to that level has thus left the oncological profession, and particularly those involved in lung cancer treatment, a void in terms of pinpointing treatments that may permit greater potential for recovery, and more accurately determining individual patients' prognoses for full recovery from cancer.

The inventive system and lymph node collection kit thus allows for the subject surgeon to easily remove and store specific mediastinal lymph nodes (that may or may not have cancerous growths present already) properly for the subject pathologist to make the most thorough analysis of the overall removed lymph node population and in terms of cancerous cell growth therein. The surgeon would diligently remove specific lymph nodes from set mediastinal locations and deposit the removed nodes within properly color-, name-, and/or number-coded collection containers correlated with staging standards set by the International Association for the Study of Lung Cancer (IASLC), the American Joint Committee on Cancer (AJCC), and the Union for International Cancer Control (UICC). Such coding (again, through color, station name, and/or station number, preferably all three simultaneously) is provided for simplicity sake as well as compliance with such a set staging standard. As well, the standards include a specific labeling system of number designations set by the IASLC that may be utilized alone or in addition to the colors on the containers as well. Such a color/station name/numeric label designation system is as follows:

TABLE

Lymph Node Staging Color and Numeric Codes

| Lymph Node Location | Color | Number |
| --- | --- | --- |
| Low cervical, supraclavicular, sternal notch | Red | 1 |
| Upper Para tracheal (right) | Violet | 2R |
| Upper Para tracheal (left) | Blue | 2L |
| Prevascular | Dark Green | 3a |
| Prevertebral (Retrotracheal) | Brown | 3p |
| Lower Para tracheal (right) | Orange | 4R |
| Lower Para tracheal (left) | Light Orange | 4L |
| Subaortic | Dark Blue | 5 |
| Para-aortic | Lime Green | 6 |
| Subcarinal | Light Blue | 7 |
| Paraesophageal | Silver | 8 |
| Pulmonary Ligament | Gold | 9 |
| Hilar | Yellow | 10 R or L |

Such designations are even further separable in terms of general station location, as well. Thus, Number 1 is considered the Supraclavicular Zone; Numbers 2-4 are considered Superior Mediastinal Nodes (further referred to as the Upper Zone); Numbers 5 and 6 are the Aortic nodes (the AP Zone); and Numbers 7, 8, and 9 are the Inferior Mediastinal Nodes, with Number 7 the Subcarinal Zone and Numbers 8 and 9 the Lower Zone; and Number 10 (R or L) part of the Hilar Zone (which includes other nodes that are usually present within a complete resected lung specimen and thus do not require inclusion within this diagnostic method and overall kit since the pathologist will already understand the location of such nodes and can remove them himself or herself from such a resected specimen). As such, the kit utilized for this inventive diagnostic procedure may be separated in some manner by any of these Node or Zone designations in addition to any other manner.

Since, as noted above, the lymph nodes at issue may not differ to any appreciable degree in appearance, it is imperative that the surgeon removing such individual nodes properly do so in a manner that allows for proper introduction within the proper collection container for the ultimate communication to the subject pathologist as to the location of each removed lymph node initially.

The collection kit itself is rather compact for ease in storage and transportation, yet with sufficient space within each individual collection container to allow introduction of and retention of any specific removed mediastinal lymph node therein. The overall kit thus includes a box with a removable lid, and twelve compartments therein to house the twelve collection containers therein. The containers may be of any suitable size that permits the user proper collection, storage, transport, and removal therefrom. As well, the containers should include a removable lid themselves, to allow placement of the subject lymph nodes within an opened container, with the subsequent cover and protection from the environment supplied by the removable lid. The lids may include the proper color and/or numeric coding for proper lymph node mediastinal location designation for communication with a pathologist of such tacit information.

The surgeon may employ any typical procedure to remove such lymph node specimens from a target patient's mediastinal region as long as he or she properly deposits such resultant materials within the appropriate collection container for transfer to a pathologist for proper analysis thereof in relation to such specific mediastinal locations. The analysis itself may be of any typical manner that assesses the degree of cancer cell presence and spread from a pathological perspective. The pathologist can then relate his or her analyses to an oncologist for proper treatment in relation to the detailed pathological results from the lymph node location issues permitted through the utilization of the system and specimen collection kit described herein.

BRIEF DESCRIPTION OF THE DRAWINGS

FIG. 1 is the IASLC lymph node staging map showing the general locations of lymph nodes in the lungs and mediastinal region of the human body.

DETAILED DESCRIPTION OF THE DRAWINGS AND PREFERRED EMBODIMENTS OF THE INVENTION

The following descriptions and drawings are not intended to limit the invention to any degree, as the overall scope of the invention should be evident through a review of the entire disclosure herein. Such descriptions and drawings thus merely provide one potential embodiment of the overall inventive system and collection kit.

Figure 2:
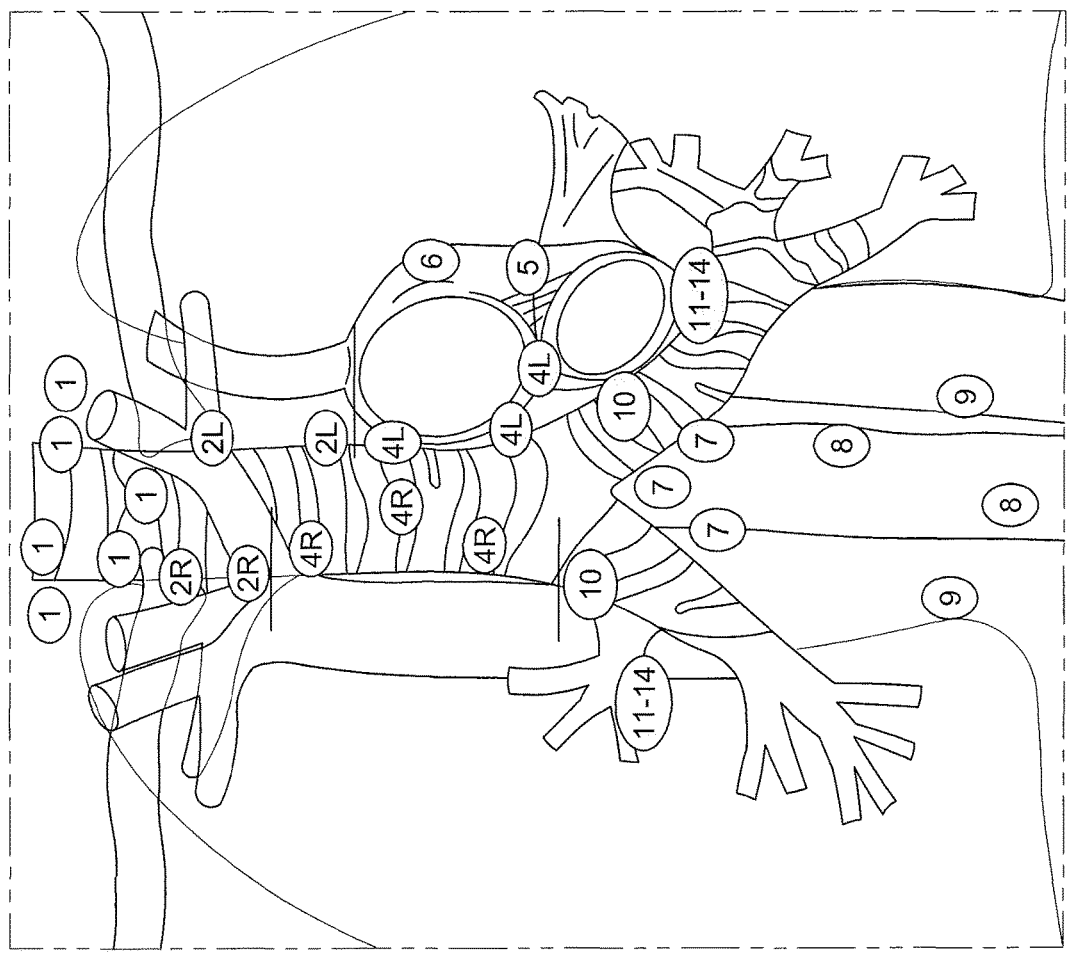
FIG. 2 is a more detailed depiction of a lymph node map of the mediastinal region.

FIGS. 1 and 2 show a cross-section of a typical mediastinal region of a human body, particularly showing a person's lungs, trachea, aorta, clavicles, bronchi, and bronchioles. Numerous lymph nodes are shown as well, in particular low cervical, supraclavicular, and sternal notch nodes 11, upper paratracheal nodes 12, 13, para-aortic nodes 15, lower paratracheal nodes 16, 17, subcarinal nodes 20, paraesophageal nodes 21, and pulmonary ligament nodes 22. Such nodes are but nine of the different stations of nodes throughout the mediastinal region that may show cancer growth and spread within a patient with lung cancer. Thus, removal of at least one such node, 12, 13, 15, 16, 17, 20, 21, 22, as well as at least one of the four other station types (FIGS. 2 through 7) and the appropriate hilar lymph node (station 10R or 10L, depending on the side where the primary tumor is located) would be undertaken by a surgeon and properly placed within the collection kit (100 of FIG. 9) via specific coded collection containers (98 of FIG. 8, 102 through 124 of FIG. 9). These particular nodes provided in effective detail in FIG. 1 would thus be deposited within the appropriate coded (or numeric-coded, or both color- and numeric-coded) container as provided in the color and numeric code table, above.

FIG. 2 shows general stations of the lung/mediastinal lymph nodes that may be removed by a surgeon for subsequent examination by a pathologist. The numbers 1-9 relate to the legend present on FIG. 1. Numbers 11-14 relate to hilar/peripheral zone lymph nodes that are typically not removed separately as all of the other types. The interlobar node 11 is located within the hilar zone and, as noted above, is typically present within resected lung specimens that are brought to the pathologist intact and with this and peripherical zone nodes intact and therein for removal by the pathologist instead of by the surgeon. Thus, 12 would be the lobar node, 13, the segmental node, and 14 the subsegemental node, all, again, part of the peripheral zone of the lung/mediastinal region of a subject patient. Closer views of the lymph nodes at issue are provided in FIGS. 3-7.

Figure 3:
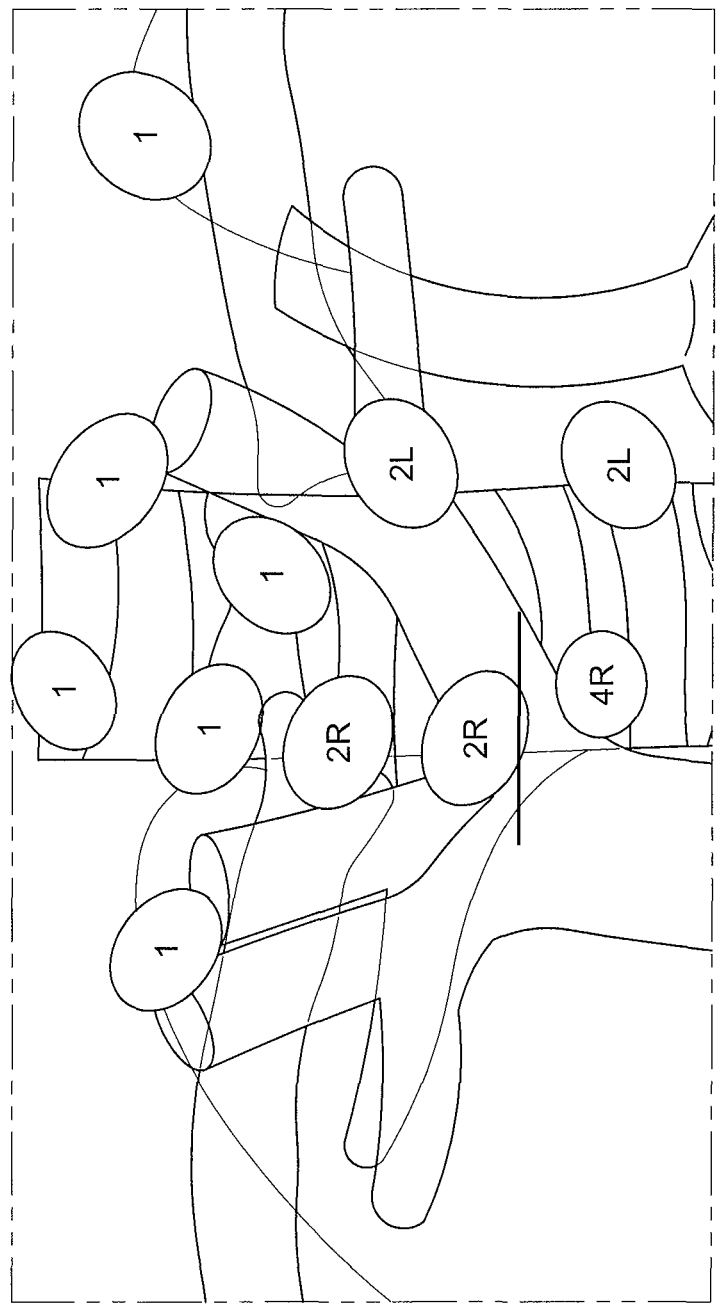
FIG. 3 depicts the supraclavicular, right upper paratracheal, and left upper paratracheal lymph nodes of a human body.
Figure 4:
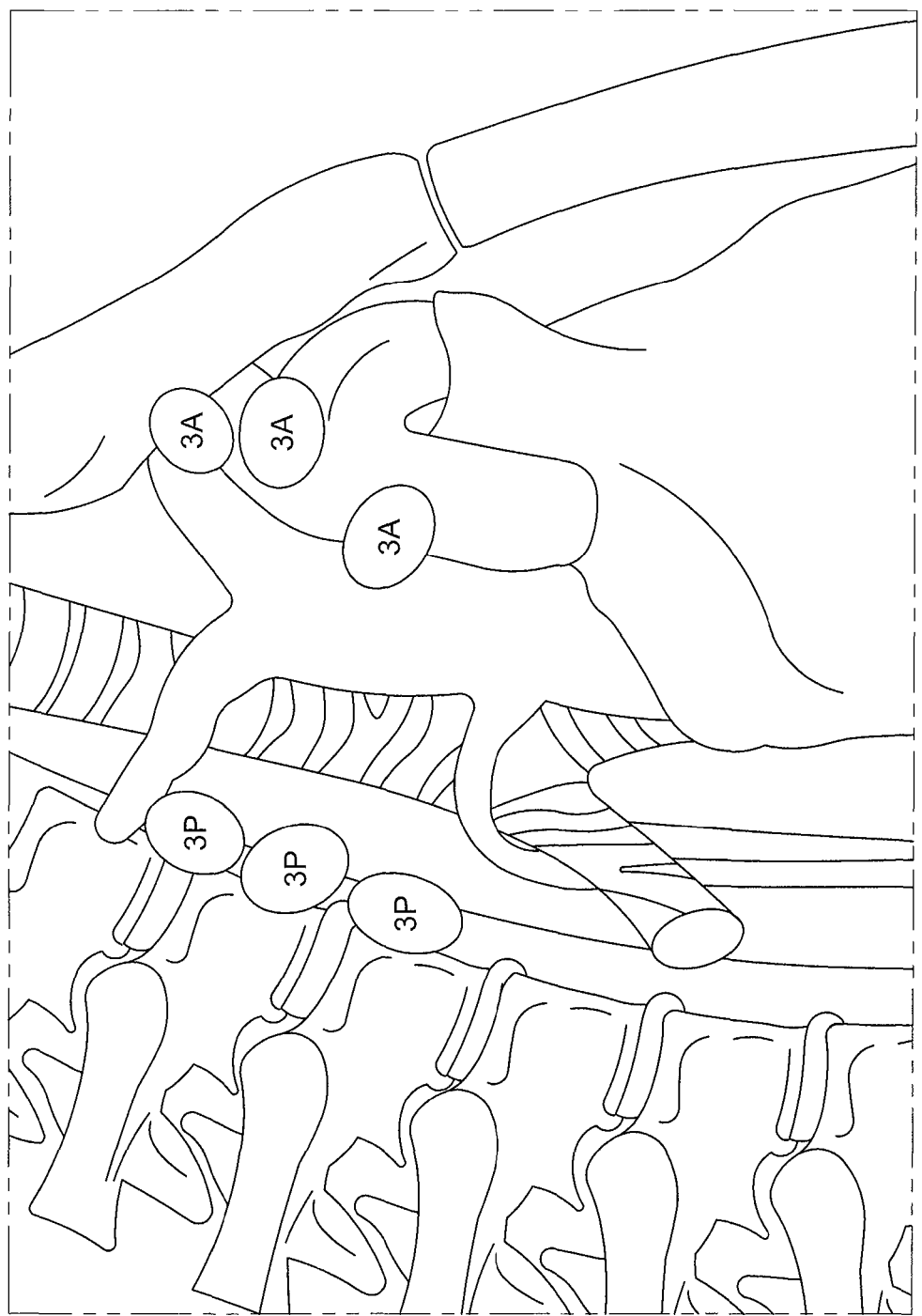
FIG. 4 depicts prevascular and prevertebral lymph nodes of a human body.
Figure 5:
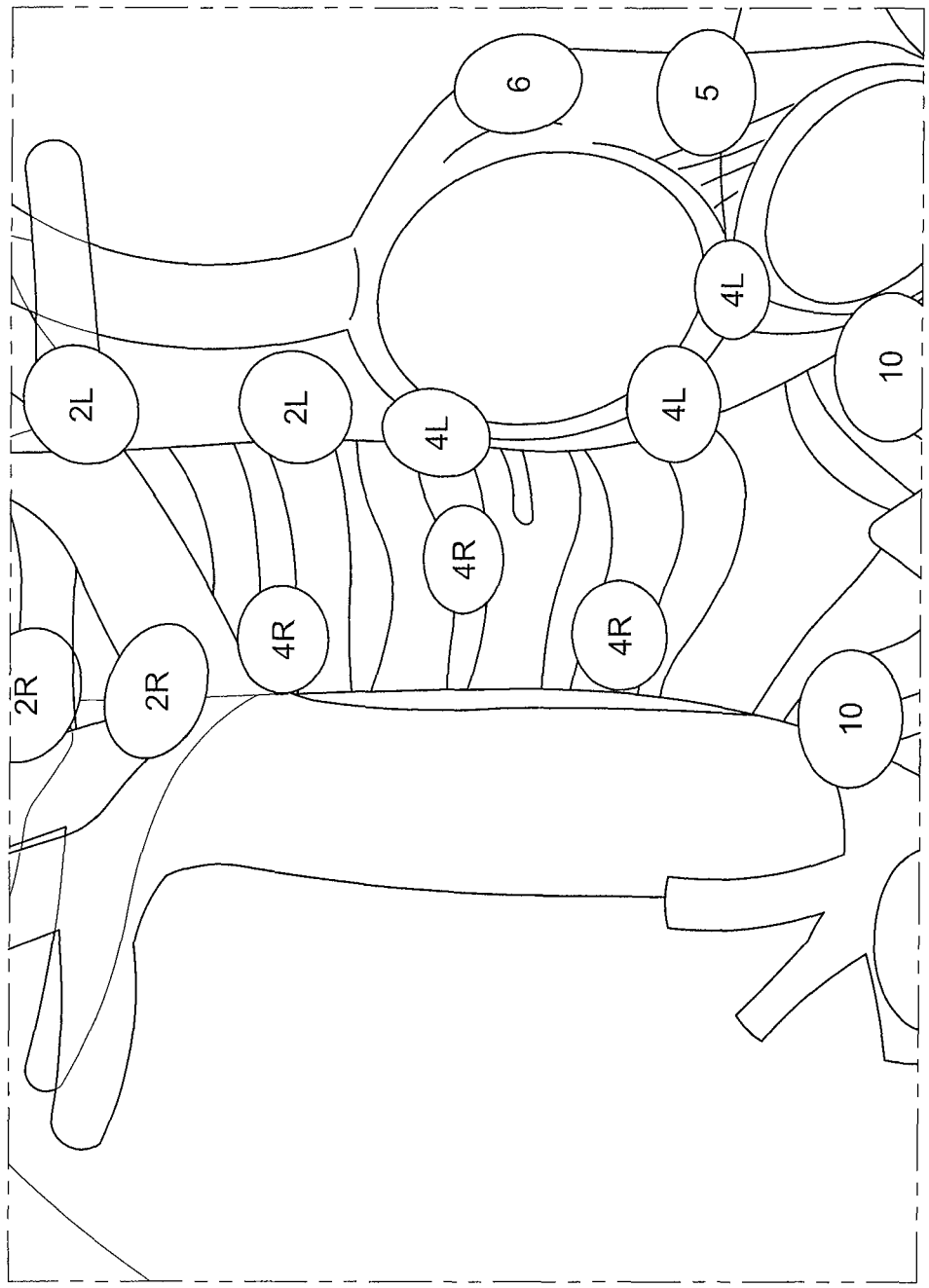
FIG. 5 depicts right lower paratracheal lymph nodes of a human body.
Figure 6:
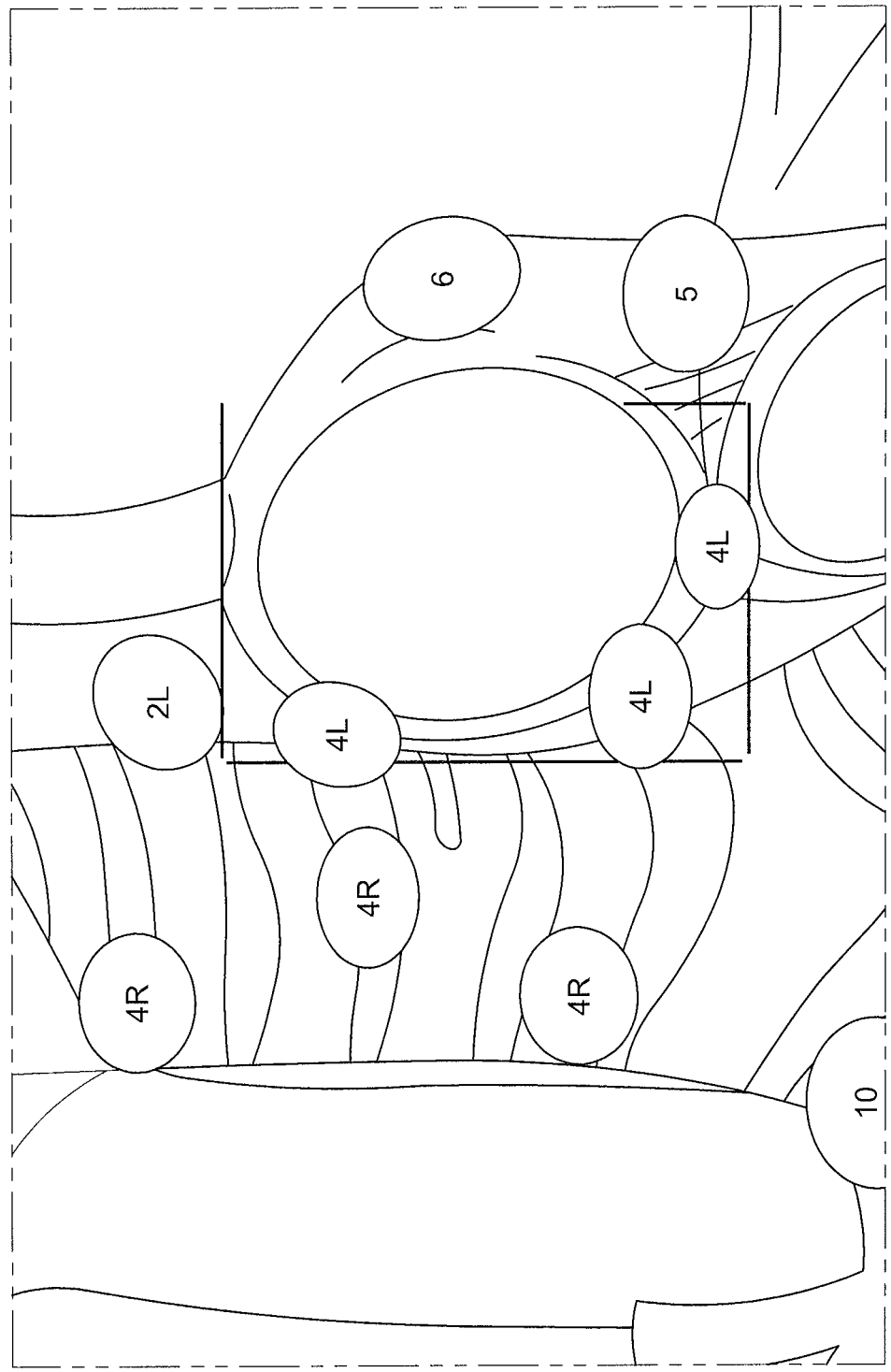
FIG. 6 depicts left lower paratracheal lymph nodes of a human body.
Figure 7:
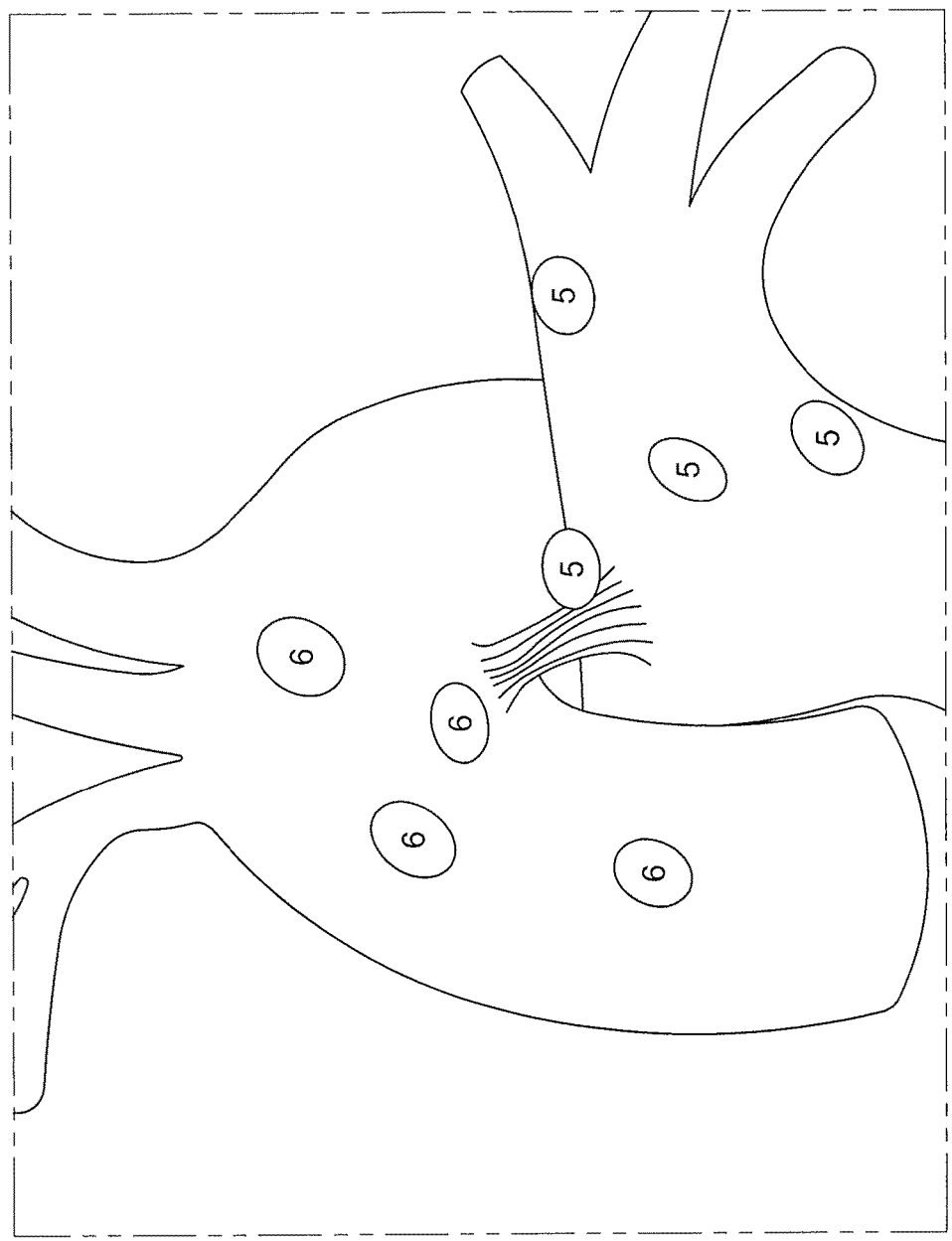
FIG. 7 depicts sub aortic and para-aortic lymph nodes of a human body.
Figure 9:
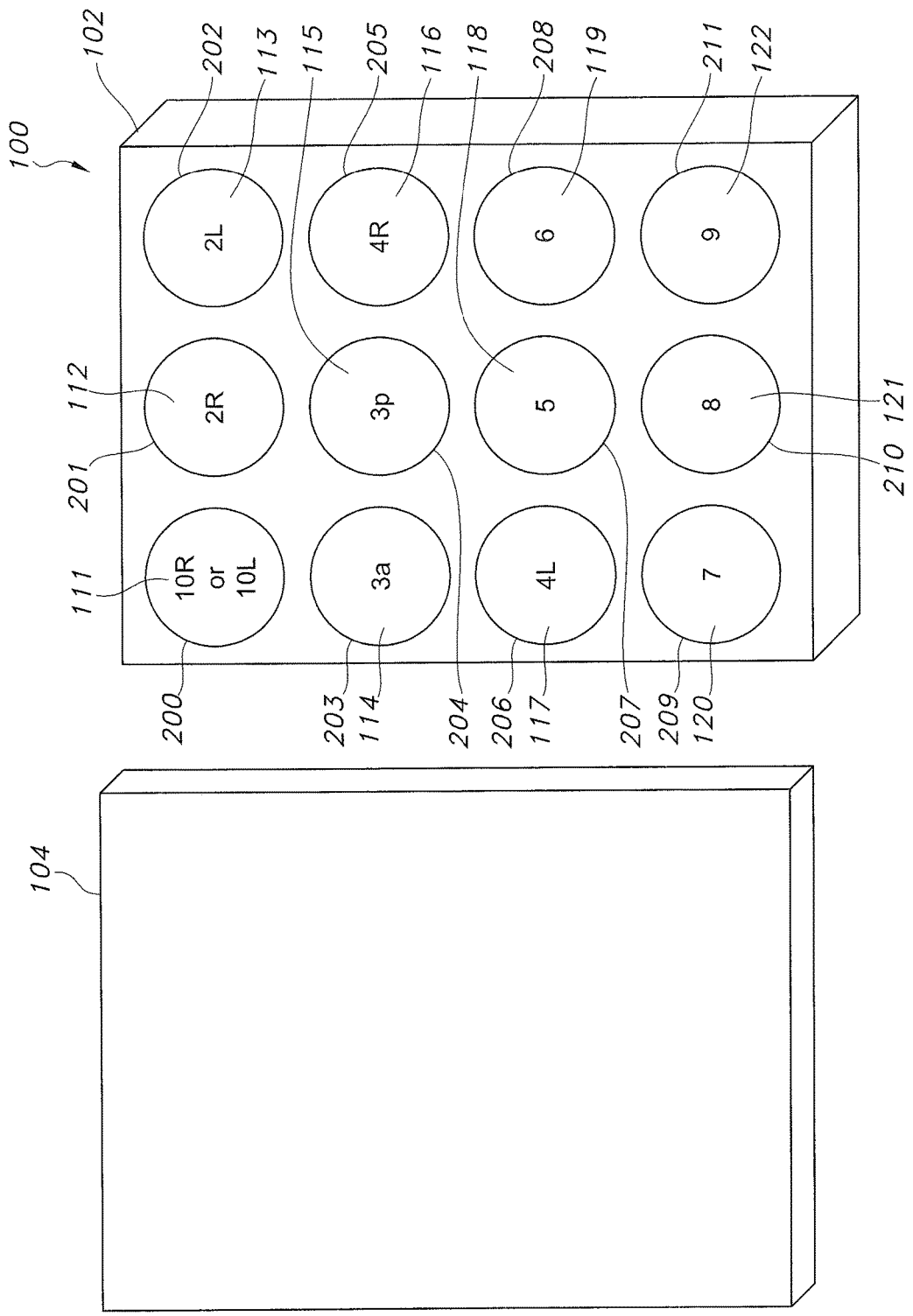
FIG. 9 depicts an aerial view of the entire collection kit.

Thus, FIG. 3 provides a more detailed view of low cervical, supraclavicular, and sternal notch node stations 1, as well as the upper paratracheal (right) 2R and upper paratracheal (left) 2L node stations. Also shown is a lower paratracheal (right) 4R node station. FIG. 4 provides a view of prevascular node stations 3A as well as retrotracheal node stations 3P from which lymph node specimens may be removed for deposit within a collection container with the proper coding (FIG. 9, for instance). As well, FIGS. 5 and 6 show the stations of right lower paratracheal nodes 4R, left lower paratracheal nodes 4L, upper paratracheal (right) nodes 2R, upper paratracheal (left) nodes 2L, a subaortic node 5, and a para-aortic node 6. As above, removal and deposit into appropriately coded collection containers would facilitate a subject pathologist's overall examination of these specific stations, as well. FIG. 7 shows closer views of the subaortic 5 and para-aortic 6 node stations for the same purpose.

Figure 8:
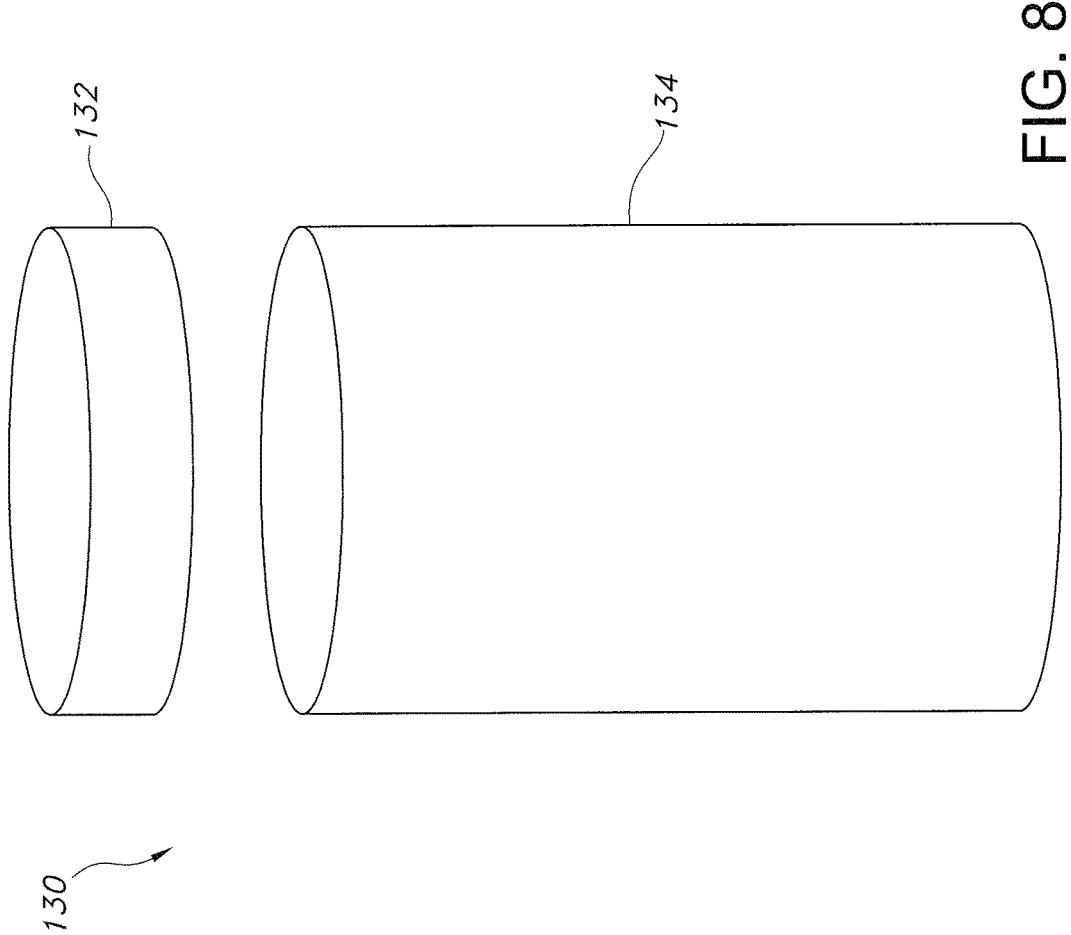
FIG. 8 depicts a side view of a typical individual collection container for introduction within the lymph node collection kit.

FIG. 8 shows a typical collection container 130 with a lid 132 and bottom container portion 134 for utilization as one of twelve such containers appropriately color-coded (as noted above) for proper deposit of different removed lymph nodes materials from specific mediastinal region stations. FIG. 9 provides a view of the entire kit 100 including a holding box 102 and a lid 104. The kit 100 includes, as well, individual collection containers 111 through 122 that fit within openings 200 through 211 within the holding box 102. Each container has its own lid (132 of FIG. 8, for instance) and the kit 100 has a secure lid 104 to ensure the containers 111 through 122 remain in place during storage and transport. As well, the containers 111-122 include numeric codes (2R, 2L, 3A, 3P, 4R, 4L, 5, 6, 7, 8, 9 and 10L or 10R)(the L and R designations may also be utilized as a manner of providing a separated kit with left, L, nodes present in one and right, R, nodes in the other, and all the other containers within each separate kit properly placed in relation to the side of the body from which each is removed without any L or R designation) to indicate the proper lymph nodes for deposit by a surgeon (color codes may also be utilized, as noted above, as well as specific station names, or combinations of any of these color, name, and number codes, including, potentially preferably, all three simultaneously) so that a pathologist may properly assess the individual nodes in relation to their mediastinal stations.

Thus, through the undertaking of an appropriate surgeon in removing mediastinal lymph nodes from a patient through a process in relation to the station of each such node sample within the patient's mediastinal region and placement of each individual station node sample within the appropriately color-coded collection container of the inventive collection kit (in relation to such a station criterium), a system that permits overall reliability and more thorough analysis of such sample node material from a station perspective is thus provided. In such a manner, the surgeon can reliably deposit removed lymph nodes within the inventive kit that then communicates to a pathologist the specific station description of the deposited materials without any further explanations from the surgeon. The pathologist then may undertake proper examination to determine the extent of possible cancer spread and/or growth throughout the patient's mediastinal region for more comprehensive understanding of the actual degree of cancer threat to the subject patient. Such results would, in turn, provide an oncologist with a more particular overview of the proper treatment course for the subject patient for more effective treatment, and hopefully, greater chance of survival and/or better quality of life thereafter.

A complete disclosure of the details and essence of this invention has been made, and the best modes of practicing it as now contemplated have been presented. It will be apparent to all skilled in the art that modifications, substitutions and additions may be made in the elements of the invention without departing from its concepts, the scope of which is defined and limited only by the ensuing claims.

The invention claimed is:

1. A mediastinal lymph node collection kit comprising multiple containers disposed within said kit each of said multiple containers pre-coded for a mediastinal station wherein each collection container of said multiple containers is coded in some manner associated with a specific station of each and every lymph node to be removed from a subject patient's mediastinal region; each of said multiple containers having an internal capacity to receive a lymph node deposit; each of said multiple containers including a preservative solution; and a removable lid to seal each container of said multiple containers, and a checklist disposed within said kit, said checklist provides for communication of removal of each and every lymph node and the placement within its appropriately pre-coded collection container and if the placement does not occur, said checklist provides a manner of indication any reason a surgeon did not place each lymph node within its appropriately coded collection container.

2. The collection kit of claim 1 wherein said kit comprises at least twelve containers and at least two separate boxes to retain and transport said twelve containers.

3. The collection kit of claim 2 wherein said at least twelve containers are removable from said kit.

4. The collection kit of claim 1 wherein said kit includes at least twelve containers and wherein said twelve containers are integrated within said kit.

5. The collection kit of claim 1 wherein each of the multiple containers are pre-coded for one of the following stations within a human patients lung/mediastinal region from which at least one lymph node is to be removed: Upper Para tracheal (right), Upper Para tracheal (left), Prevascular, Prevertebral (Retrotracheal), Lower Para tracheal (right), Lower Para tracheal (left), Subaortic, Para-artic, Subcarinal, Paraesophageal, Pulmonary Ligament, and Hilar.

6. The collection kit of claim 1 wherein said checklist further comprises a list of mandatory lymph node stations that require removal of specimens.

7. The collection kit of claim 1 wherein said kit further comprises a checklist for a pathologist.

8. The collection kit of claim 1 wherein each of said multiple containers pre-coded for a mediastinal station is coded with a code selected from the group consisting of: color, number location name, and combinations thereof.

9. The collection kit of claim 1 wherein the removable lid comprises a code and the code is selected from the group consisting of: color, number and location name and combinations thereof.

* * * * *